United States Patent
Hirama et al.

(10) Patent No.: US 10,959,959 B2
(45) Date of Patent: Mar. 30, 2021

(54) LOW-SUBSTITUTED HYDROXYPROPYL CELLULOSE AND SOLID PREPARATION

(71) Applicant: SHIN-ETSU CHEMICAL CO., LTD., Tokyo (JP)

(72) Inventors: Yasuyuki Hirama, Joetsu (JP); Naosuke Maruyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/667,307

(22) Filed: Aug. 2, 2017

(65) Prior Publication Data

US 2018/0049990 A1 Feb. 22, 2018

(30) Foreign Application Priority Data

Aug. 16, 2016 (JP) .............................. JP2016-159639

(51) Int. Cl.
| | |
|---|---|
| *A61K 9/50* | (2006.01) |
| *C08B 3/00* | (2006.01) |
| *C08J 3/12* | (2006.01) |
| *A61K 9/16* | (2006.01) |
| *A61K 47/38* | (2006.01) |
| *A61K 9/20* | (2006.01) |
| *C08B 11/08* | (2006.01) |

(52) U.S. Cl.
CPC .......... *A61K 9/5047* (2013.01); *A61K 9/1652* (2013.01); *A61K 9/2054* (2013.01); *A61K 47/38* (2013.01); *C08B 3/00* (2013.01); *C08B 11/08* (2013.01); *C08J 3/12* (2013.01)

(58) Field of Classification Search
CPC .................................................. A61K 9/5047
See application file for complete search history.

(56) References Cited

U.S. PATENT DOCUMENTS

| 6,380,381 B1 | 4/2002 | Obara |
|---|---|---|
| 2008/0039621 A1 | 2/2008 | Maruyama et al. |
| 2010/0323006 A1 | 12/2010 | Nakagawa et al. |

FOREIGN PATENT DOCUMENTS

| EP | 2112169 A1 | 10/2009 |
|---|---|---|
| JP | H10-279601 A | 10/1998 |
| JP | 2001-031701 A | 2/2001 |
| JP | 2008-133432 A | 6/2008 |

OTHER PUBLICATIONS

Jan. 4, 2018 Extended European Search Report issued in Patent Application No. 17185533.1.
Nakagami, H et al., "In Vitro Evaluation of Micronized Low-Substituted Hydroxypropylcellulose as an Insoluble Swellable Matrix for Sustained-Release Tablets.", Drug Design and Discovery, Taylor & Francis Inc., US, vol. 8, No. 2, pp. 103-116, (1991).
Shin Etsu, "Low-Substituted Hydroxypropyl Cellulose NF L-HPC.", XP055434172, http://www.elementoorganika.ru/files/1hpc.pdf, (2005).
Jan. 6, 2020 Office Action issued in Chinese Patent Application No. 201710701990.5.
Quinten et al., "Development of injection moulded matrix tablets based on mixtures of ethylcellulose and low-substituted hydroxypropylcellulose," European Journal of Pharmaceutical Sciences, No. 37, pp. 207-216, 2009.
Nov. 23, 2020 Office Action issued in Indian Patent Application No. 201714028734.

*Primary Examiner* — Gina C Justice
(74) *Attorney, Agent, or Firm* — Oliff PLC

(57) ABSTRACT

Provided is low-substituted hydroxypropyl cellulose from which a granulation product having an adequate particle size can be obtained in a wet granulation method and a tablet having excellent compactibility and disintegrability can be obtained. More specifically, provided is low-substituted hydroxypropyl cellulose having a hydroxypropoxyl content of from 5 to 16% by weight and a water-soluble content of less than 2% by weight, wherein a weight ratio of water to the low-substituted hydroxypropyl cellulose giving a maximum torque is from 3 to 5 as determined while adding one part by weight of water per minute to one part by weight of the low-substituted hydroxypropyl cellulose under mixing with biaxial mixing blades. Also provided are a solid preparation including the low-substituted hydroxypropyl cellulose, and the like.

8 Claims, No Drawings

LOW-SUBSTITUTED HYDROXYPROPYL CELLULOSE AND SOLID PREPARATION

BACKGROUND OF THE INVENTION

1. Field of the Invention

The invention relates to low-substituted hydroxypropyl cellulose having good compactibility and disintegrability, which is added to a solid preparation as a disintegrator or binder in the fields of pharmaceuticals and food.

2. Description of the Related Art

A solid preparation as a pharmaceutical or food disintegrates as a disintegrant contained therein absorbs water and swells therewith. Examples of the disintegrant include low-substituted hydroxypropyl cellulose, carboxymethyl cellulose and calcium a salt thereof, and a starch and a derivative thereof.

Particularly in the fields of pharmaceuticals, unstable drugs are increasing among newly developed drugs and additives usable for them are limited from the standpoint of mutual action between them. Under such situations, low-substituted hydroxypropyl cellulose has been used popularly as a nonionic disintegrant or binder so that it may be regarded as an preferable additive.

A tablet is one of the dosage forms of solid preparations as pharmaceuticals or food. It is a solid preparation obtained by compressing powder into a certain shape. This dosage form has advantages such as handling ease so that its percentage in the total production amount of pharmaceuticals is about 50%, showing that it is the most popularly used dosage form.

Examples of the method of producing a tablet include a dry direct tableting method, a dry granulation tableting method, an extrusion granulation tableting method, and a wet granulation tableting method. Compared with the dry direct tableting method in which a mixture of a drug, an excipient and the like is tableted as is, the wet granulation tableting method comprises complex steps, but it is more popularly used because a granulation operation contributes to improvement in compactibility and flowability of powder, and uniformity of drug content. The wet granulation tableting method comprises the steps of: granulating a mixture of a drug, an excipient and the like by using a proper solvent such as a binder solution or water and then drying to obtain a granulation product, and tableting the granulation product into a tablet. The wet granulation tableting method further includes a wet mixing granulation tableting method using an agitation granulator and a fluidized bed granulation tableting method using a fluidized bed granulator.

JP 2001-31701A discloses that when low-substituted hydroxypropyl cellulose having a specified water-soluble content and the like is used in the extrusion granulation method, granulation products having preferable disintegrability can be obtained, while it is used in the fluidized-bed granulation method, granulation products having a large bulk density can be obtained.

JP 10-279601A discloses that when low-substituted hydroxypropyl cellulose having an apparent average polymerization degree within a predetermined range is used in the wet mixing granulation tableting method, good granulation characteristics and tablet performance can be obtained.

SUMMARY OF THE INVENTION

When the low-substituted hydroxypropyl cellulose described in JP 2001-31701A is used in the fluidized bed granulation method, however, granulation is sometimes accelerated excessively so that a further improvement in disintegration time of the granulation product is demanded. When it is used in the extrusion granulation method, a further improvement in the granulation rate or disintegration time of the granulation product is demanded.

When the low-substituted hydroxypropyl cellulose described in JP 10-279601A is used in the wet mixing granulation tableting method, granulation is sometimes accelerated excessively even if the low-substituted hydroxypropyl cellulose has an equal apparent average polymerization degree. Thus, there is a demand for further improvement in variation in the tablet weight during tableting or in disintegration time of the obtained tablet.

The invention has been made to overcome the above-described drawbacks of the related art. An object is to provide low-substituted hydroxypropyl cellulose from which a granulation product having an adequate particle size can be obtained in a wet granulation method, and from which a tablet excellent in compactibility and disintegrability can be obtained.

The inventors have carried out an extensive investigation with a view to achieving the above-descried object. As a result, it has been found that low-substituted hydroxypropyl cellulose powder obtained by removing small particles therefrom has sufficient compactibility and excellent disintegrability, leading to completion of the invention.

In one aspect of the invention, there is provided low-substituted hydroxypropyl cellulose having a hydroxypropoxyl content of from 5 to 16% by weight and a water-soluble content of less than 2% by weight, wherein a weight ratio of water to the low-substituted hydroxypropyl cellulose giving a maximum torque is from 3 to 5 as determined while adding one part by weight of water per minute to one part by weight of the low-substituted hydroxypropyl cellulose under mixing with biaxial mixing blades.

In another aspect of the invention, there is also provided a solid preparation comprising the low-substituted hydroxypropyl cellulose.

In a further aspect of the invention, there is also provided a method for producing low-substituted hydroxypropyl cellulose, comprising the steps of: pulverizing starting material low-substituted hydroxypropyl cellulose having a hydroxypropoxyl content of from 5 to 16% by weight into low-substituted hydroxypropyl cellulose powder having a volume-average particle size of from 30 to 100 μm as measured a dry laser diffraction method, and classifying the low-substituted hydroxypropyl cellulose powder to remove therefrom small particles having a volume-average particle size of less than 30 μm as measured by a dry laser diffraction method.

In a still further aspect of the invention, there is also provided a method for producing a granulation product of the low-substituted hydroxypropyl cellulose, comprising the steps of: blending the low-substituted hydroxypropyl cellulose, a drug, and water or a water-soluble binder solution to obtain a mixture, and granulating the mixture.

According to the present invention, the low-substituted hydroxypropyl cellulose has good compactibility and disintegrability so that a solid preparation comprising the low-substituted hydroxypropyl cellulose can have a reduced disintegration time and a rapid drug effect. When it is used in the wet granulation method, a granulation product having an adequate particle size can be produced.

DETAILED DESCRIPTION OF THE PREFERRED EMBODIMENTS

The weight ratio of water to low-substituted hydroxypropyl cellulosed giving a maximum torque, which may also be referred to as "maximum-torque-generating ratio", is determined by measuring, by means of an absorption tester "S-500" (product of ASAHISOUKEN), a change in torque when water is added to 5.0 g of low-substituted hydroxypropyl cellulose at a dropping rate of 5.0 g/min while mixing with biaxial mixing blade, and dividing the amount of water at the maximum torque by the weight (5.0 g) of the low-substituted hydroxypropyl cellulose. The mixing blade on one axis of the two axes has a rotational speed of 60 rpm (peripheral velocity of about 0.72 m/min) and the mixing blade on the other axis has a rotational speed of 30 rpm (peripheral velocity of about 0.36 m/min). Since low-substituted hydroxypropyl cellulose is hygroscopic, it is dried prior to the measurement by allowing it to stand at 105° C. for 2 hours.

The maximum-torque-generating ratio corresponds to the maximum torque generated when the water absorption and water retention of low-substituted hydroxypropyl cellulose reach the maximum level. After the maximum torque is generated, the low-substituted hydroxypropyl cellulose cannot have further water absorption and water retention so that it becomes slurry, thereby decreasing the torque.

According to the invention, the weight ratio of water to low-substituted hydroxypropyl cellulose giving a maximum torque as determined while adding one part by weight of water per minute to one part by weight of low-substituted hydroxypropyl cellulose under mixing with biaxial mixing blades, is from 3 to 5, preferably from 3.2 to 4.8, more preferably from 3.4 to 4.7. When the maximum-torque-generating ratio is less than 3, granulation is accelerated excessively in the wet granulation method. The granulation product thus obtained has an increased particle size and increased strength so that a tablet obtained by tableting the granulation product has a prolonged disintegration time. When the maximum-torque-generating ratio is more than 5, the granulation does not proceed sufficiently in the wet granulation method. The granulation product thus obtained has a small particle size and insufficient strength so that a tablet obtained by tableting the granulation product has reduced hardness.

The low-substituted hydroxypropyl cellulose having a maximum-torque-generating ratio within the above-described range can be obtained, for example, by removal of small particles as described later.

The water-soluble content can be measured by the method comprising the steps of: dispersing 5.0 g of low-substituted hydroxypropyl cellulose which has been dried as described above, in 100 mL of water of 25° C. to obtain a dispersion; shaking the dispersion for 30 minutes; centrifuging the shaken dispersion by a centrifugal separator at a centrifugal force of about 1650×g for 20 minutes to obtain a supernatant; and evaporating 30 mL of the supernatant transferred into a container to dryness. The water-soluble content is determined by the following formula:

Water-soluble content={(weight of container after evaporation to dryness−weight of empty container)×100/30/5}×100

The water-soluble content of the low-substituted hydroxypropyl cellulose is less than 2% by weight, preferably less than 1.8% by weight, more preferably less than 1.5% by weight. A water-soluble component dissolves during granulation to have action similar to that of a sizing agent (i.e. a binder) so that when the water-soluble content is 2% by weight or more, granulation is accelerated excessively in the wet granulation method. The granulation product thus obtained has an increased particle size. In addition, the granulation product inhibits water conduction so that a tablet obtained by tableting the granulation product has a prolonged disintegration time. The lower limit of the water-soluble content is preferably as small as possible. For example, removal of the small particles, which will be described later, usually does not result in reduction of the water-soluble content to 0% by weight, but the water-soluble content of more than 0% by weight.

The low-substituted hydroxypropyl cellulose has a hydroxypropoxyl content of from 5 to 16% by weight, preferably from 6 to 15% by weight, more preferably from 7 to 14% by weight. The hydroxypropoxyl content of less than 5% by weight reduces swelling properties after water absorption. The hydroxypropoxyl content of more than 16% by weight increases the water solubility of the hydroxypropyl cellulose so that a solid preparation comprising it does not have sufficient disintegrability. The hydroxypropoxyl content can be determined in accordance with the quantitative method described in the "low-substituted hydroxypropyl cellulose" of the Japanese Pharmacopoeia Seventeenth Edition.

The low-substituted hydroxypropyl cellulose absorbs water and swells, but does not dissolve in water. It dissolves in an aqueous alkali solution. By making use of such a property, the length of the molecular chain of the low-substituted hydroxypropyl cellulose can be evaluated conveniently from an alkali viscosity.

The alkali viscosity can be determined using a single cylinder rotational viscometer (Brookfield viscometer). The alkali viscosity means a viscosity at 20° C. obtained by the method comprising the steps of: dispersing 6.0 g of low-substituted hydroxypropyl cellulose which has been dried as described above, in 144 g of water of 20° C. to obtain a dispersion; subjecting the dispersion to addition of 150 g of a 20% by weight aqueous sodium hydroxide solution of 20° C. while being stirred to obtain a low-substituted hydroxypropyl cellulose solution; and measuring the viscosity of the solution by a Brookfield viscometer ("TVB10 type viscometer", product of Toki Sangyo).

The alkali viscosity at 20° C. of the 2% by weight solution of low-substituted hydroxypropyl cellulose in a 10% by weight aqueous sodium hydroxide solution is preferably from 20 to 120 mPa·s, more preferably from 30 to 110 mPa·s, still more preferably from 40 to 100 mPa·s from the standpoint of suitability of granulation during the wet granulation and disintegrability and compactibility of the granulation product.

According to the invention, the low-substituted hydroxypropyl cellulose has a volume-average particle size, as measured by a dry laser diffraction method, of preferably from 30 to 100 μm, more preferably from 40 to 80 μm, still more preferably from 45 to 70 μm from the standpoint of disintegrability and compactibility. The volume-average particle size means a diameter corresponding to the 50% cumulative value of a volume-based cumulative distribution curve. The diameter corresponding to the 50% cumulative value of a volume-based cumulative distribution curve can be measured, for example, by a laser diffraction type particle-size distribution analyzer "Mastersizer 3000" (product of Malvern) based on the Fraunhofer diffraction theory under the conditions of a dispersing pressure of 2 bar and scattering intensity of from 2 to 10%.

The low-substituted hydroxypropyl cellulose can be used as a binder or disintegrant for a solid preparation such as a tablet, granules, fine granules and a capsule. It is particularly suited for the tablet, which is a dosage form easy to handle and most popularly used. The tablet can be obtained by any one of a dry direct tableting method, a wet mixing granulation tableting method, a fluidized bed granulation tableting method, and a dry granulation tableting method. The wet mixing granulation tableting method or the fluidized bed granulation tableting method is particularly suited because the uniformity of drug content can be easily maintained.

The content of the low-substituted hydroxypropyl cellulose in a solid preparation is preferably from 2 to 50% by weight, more preferably from 5 to 30% by weight, still more preferably from 5 to 20% by weight from the standpoint of compactibility, disintegrability and storage stability.

Production of a tablet comprising the low-substituted hydroxypropyl cellulose by the wet mixing granulation tableting method will next be described. The tablet can be produced by the method comprising the steps of: blending the low-substituted hydroxypropyl cellulose, a drug, and water or a water-soluble binder solution to obtain a first mixture, granulating the first mixture by an agitation granulator to obtain a granulation product, drying the granulation product, mixing the dried granulation product with a small amount of a lubricant to obtain a second mixture, and then tableting the second mixture under a predetermined pressure by a tableting machine.

The granulation product not subjected to tableting (i.e. the granulation product obtained by the wet granulation method) corresponds to granules or fine granules. A capsule can be produced by encapsulation of the granules or fine granules.

The average particle size of the granulation product to be tableted can be determined by the analytical sieving method described in "General Tests" of the Japanese Pharmacopoeia Seventeenth Edition. The average particle size of the granulation product to be tableted is preferably from 50 to 400 μm, more preferably from 100 to 350 μm, still more preferably from 150 to 300 μm from the standpoint of reduction of tableting troubles, filling suitability of the granulation product into a mortar of a tableting machine, and low variation in the weight of tablets.

The size of the tablet can be selected freely. From the standpoint of handling ease and swallowing ease, the diameter of the tablet is preferably from 6 to 12 mm and the weight of the tablet is preferably from 70 to 700 mg per tablet.

A tableting pressure during tableting is preferably from 50 to 300 MPa from the standpoint of tablet hardness and reduction of tableting troubles.

The tablet hardness can be determined by the maximum breaking strength at which a tablet is broken when a load is applied at a constant rate to the diameter direction of the tablet. It can be measured, for example, using a tablet hardness tester ("TBH-125", product of ERWEKA). The hardness of the tablet is preferably from 40 to 120N, more preferably from 45 to 100N, still more preferably from 50 to 90N from the standpoint of durability and disintegrability.

The disintegration time of the tablet can be determined in accordance with "Disintegration Test" (test liquid: water, without auxiliary disk) of the Japanese Pharmacopoeia Seventeenth Edition. The disintegration time of the tablet is preferably within 15 minutes, more preferably within 10 minutes, more preferably within 5 minutes from the standpoint of exerting a drug effect.

According to the invention, the drug usable for the solid preparation containing the low-substituted hydroxypropyl cellulose is not particularly limited insofar as it is an orally administrable drug. Examples of such a drug include a central nervous system drug, a circulatory system drug, a the respiratory system drug, a digestive system drug, an antibiotic, an antitussive and expectorant drug, an antihistamine drug, an analgesic antipyretic anti-inflammatory drug, a diuretic drug, an autonomic drug, an antimalarial drug, an antidiarrheal drug, a psychotropic drug, and vitamins and derivatives thereof.

Examples of the central nervous system drug include diazepam, idebenone, naproxen, piroxicam, indomethacin, sulindac, lorazepam, nitrazepam, phenytoin, acetaminophen, ethenzamide, ketoprofen, and chlordiazepoxide.

Examples of the circulatory system drug include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, and alprenolol hydrochloride.

Examples of the respiratory system drug include amlexanox, dextromethorphan, theophilline, pseudo-ephedrine, salbutamol, and guaiphenesin.

Examples of the digestive system drug include benzimidazole-based drugs having anti-ulcer action such as 2-[(3-methyl-4-(2,2,2-trifluoroethoxy)-2-pyridyl)methylsulfinyl] benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cephaclor, and erythromycin.

Examples of the antitussive and expectorant drug include noscapine hydrochloride, carbetapentane citrate, isoaminile citrate, and dimemorfan phosphate.

Examples of the antihistamine drug include chlorpheniramine maleate, diphenhydramine hydrochloride, and promethazine hydrochloride.

Examples of the analgesic antipyretic and anti-inflammatory drug include ibuprofen, diclofenac sodium, flufenamic acid, sulpyrine, and aspirin.

Examples of the diuretic drug include caffeine.

Examples of the autonomic drug include dihydrocodeine phosphate, methylephedrine dl-hydrochloride, atropine sulfate, acetylcholine chloride, and neostigmine.

Examples of the antimalarial drug include quinine hydrochloride.

Examples of the antidiarrheal drug include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

In the production of a solid preparation containing the low-substituted hydroxypropyl cellulose, a disintegrant, a binder, an extender, a taste corrigent component, a flavor, a lubricant or the like, which is ordinarily used for solid preparations, may be added in an ordinary amount.

Examples of the disintegrant include corn starch, potato starch, partially pregelatinized starch, carboxymethyl starch sodium, carmellose, croscarmellose sodium, crystalline cellulose, and crospovidone.

Examples of the binder include hydroxypropyl cellulose, polyvinylpyrrolidone, and hydroxypropylmethyl cellulose.

Examples of the extender include erythritol, mannitol, sorbitol, lactose, sucrose, calcium phosphate, and calcium sulfate.

Examples of the taste corrigent component include citric acid, tartaric acid, and malic acid.

Examples of the flavor include menthol, peppermint oil, and vanillin.

Examples of the lubricant include magnesium stearate and sucrose fatty acid esters.

The low-substituted hydroxypropyl cellulose may be produced as follows: First, sodium hydroxide is caused to act on raw material pulp to obtain alkali cellulose. The alkali cellulose may be obtained, for example, by immersing sheet-like pulp in an aqueous sodium hydroxide solution and then squeezing the resulting pulp, or by spraying an aqueous sodium hydroxide solution to pulp powder under stirring. Then, the alkali cellulose is reacted with propylene oxide for a substitution reaction. Subsequently, sodium hydroxide remaining in the reaction product is neutralized with an acid such as acetic acid or hydrochloric acid. Then, the reaction product is washed, dried, and pulverized. The pulverization is carried out, for example, by using an impact pulverizer such as a hammer mill or an impact mill, or a compaction pulverizer such as a roller mill or a ball mill. The pulverized low-substituted hydroxypropyl cellulose is classified to remove small particles therefrom. As a result, the intended low-substituted hydroxypropyl cellulose can be produced.

The pulverized low-substituted hydroxypropyl cellulose sometimes contains small particles attributable to excessive pulverization. Conventionally, it is considered that the water-soluble component is distributed uniformly in the pulverized low-substituted hydroxypropyl cellulose, regardless of the particle size, so that there is no difference in the water-soluble content between small and large particles. However, it has been surprisingly found that small particles in the pulverized low-substituted hydroxypropyl cellulose have a large water-soluble content and a low maximum-torque-generating ratio. It has been also found that for this reason, granulation is accelerated excessively in the wet granulation, which will result in delay in disintegration time, and as the small particles increases, the water-soluble content increases and the maximum-torque-generating ratio decreases.

Accordingly, in the invention, by classifying the pulverized low-substituted hydroxypropyl cellulose to remove small particles therefrom, the low-substituted hydroxypropyl cellulose thus obtained can have good suitability of granulation and disintegrability.

In classification, it is the common practice to remove large particles and leave only particles having particle sizes not more than a predetermined one. According to the invention, examples of the classification method include a method of dividing the pulverized low-substituted hydroxypropyl cellulose into small particles and large particles for obtaining the large particles by using a centrifuge type air classifier; a method of sieving the pulverized low-substituted hydroxypropyl cellulose for collecting the residue on the sieve; a method of capturing small particles through a bag filter for obtaining the large particles; and a combination thereof.

Further, before or after the classification, it is preferable to sieve the pulverized low-substituted hydroxypropyl cellulose by a conventional method to remove large particles generated as a result of insufficient pulverization. In this case, the sieve has an opening of preferably from 75 to 180 µm.

Small particles to be removed from the pulverized low-substituted hydroxypropyl cellulose by the classification have a volume-average particle size, as measured by the dry laser diffraction method, of preferably less than 30 µm, more preferably less than 20 µm, more preferably less than 10 µm.

Removal of the small particles having an average particle size of less than 30 µm can result in a decrease in the water-soluble content in the pulverized low-substituted hydroxypropyl cellulose and an increase in the maximum-torque-generating ratio. On the other hand, removal of the pulverized low-substituted hydroxypropyl cellulose having an average particle size of 30 µm or more is impractical because there is not a large room for reducing the water-soluble content in the pulverized low-substituted hydroxypropyl cellulose or for increasing the maximum-torque-generating ratio and also because it largely reduces a production yield.

EXAMPLES

The invention will hereinafter be described specifically with reference to Examples and Comparative Examples. It should not be construed that the invention is limited to or by Examples below.

Example 1

Alkali cellulose containing 24.5% by weight sodium hydroxide was obtained by immersing pulp in a 49% by weight aqueous sodium hydroxide solution and squeezing the resulting pulp. After the alkali cellulose was left to stand at room temperature for 8 hours, 100 parts by weight of the alkali cellulose was placed in a reactor. The reactor was purged with nitrogen and then charged with 9.5 parts by weight of propylene oxide. The resulting mixture was reacted at 40° C. for one hour, 50° C. for one hour, and 70° C. for one hour while stirring to obtain 109.5 parts by weight of a reaction product. The reaction product was introduced, for neutralization, into in 2000 parts by weight of hot water of 95° C. containing acetic acid in an amount equivalent to that of sodium hydroxide co-existing with the reaction product, followed by dehydration by squeezing to obtain a crude low-substituted hydroxypropyl cellulose product. The crude product thus obtained was washed with 3000 parts by weight of hot water of 90° C., dehydrated by squeezing, and then dried. The dried product was pulverized in a high-speed rotation impact pulverizer to obtain the pulverized product. The pulverized product was sifted through a sieve having an opening of 150 µm to collect an undersize fraction. The undersize fraction was then sifted through a sieve having an opening of 38 µm to collect an oversize fraction as the low-substituted hydroxypropyl cellulose shown in Table 1. The average particle size of the low-substituted hydroxypropyl cellulose shown in Table 1 is a volume-average particle size measured by a dry laser diffraction method.

The low-substituted hydroxypropyl cellulose thus obtained was analyzed for a water-soluble content, a maximum-torque-generating ratio, the average particle size, alkali viscosity, and an average particle size of the granulation product. The results are shown in Table 1.

Example 2

A pulverized product of low-substituted hydroxypropyl cellulose was obtained in the same manner as in Example 1, and sifted through a sieve having an opening of 150 µm to collect an undersize fraction. The undersize fraction was then sifted through a sieve having an opening of 32 µm to collect an oversize fraction as the low-substituted hydroxypropyl cellulose shown in Table 1.

Example 3

The low-substituted hydroxypropyl cellulose shown in Table 1 was obtained in the same manner as in Example 1 except that the amount of propylene oxide charged was changed to 6.9 parts by weight.

Example 4

The low-substituted hydroxypropyl cellulose shown in Table 1 was obtained in the same manner as in Example 1 except that the amount of propylene oxide charged was changed to 12.1 parts by weight.

Comparative Example 1

A pulverized product of low-substituted hydroxypropyl cellulose was obtained in the same manner as in Example 1, and sifted through a sieve having an opening of 150 μm to collect an undersize fraction. The undersize fraction was then sifted through a sieve having an opening of 25 μm to collect an oversize fraction as the low-substituted hydroxypropyl cellulose shown in Table 1.

Comparative Example 2

A crude product of low-substituted hydroxypropyl cellulose product was obtained in the same manner as in Example 1, and washed with 6000 parts by weight of hot water of 90° C. Then, the washed product was treated in the same manner as in Example 1 to obtain a pulverized product of low-substituted hydroxypropyl cellulose. The pulverized product was sifted through a sieve having an opening of 75 μm to collect an undersize fraction as the low-substituted hydroxypropyl cellulose shown in Table 1 was obtained.

Comparative Example 3

A pulverized product of low-substituted hydroxypropyl cellulose was obtained in the same manner as in Example 1, and sifted through a sieve having an opening of 75 μm to collect an undersize fraction as the low-substituted hydroxypropyl cellulose shown in Table 1.

Comparative Example 4

Alkali cellulose was obtained in the same manner as in Example 1, left to stand at 40° C. for 24 hours, and treated in the same manner as in Example 1 to obtain a pulverized product of low-substituted hydroxypropyl cellulose. The pulverized product was sifted through a sieve having an opening of 75 μm to collect an undersize fraction as the low-substituted hydroxypropyl cellulose shown in Table 1.

Tablets were produced using the low-substituted hydroxypropyl cellulose obtained in Examples and Comparative Examples by the wet mixing granulation tableting method described below. The tablet hardness and disintegration time of the tablets were measured.

(1) Wet Mixing Granulation

An mixing granulator ("VG-05", product of Powrex Corporation) was charged with 80 g of ethenzamide ("Ethenzamide PPT", product of Hachidai Pharmaceutical), 40 g of the low-substituted hydroxypropyl cellulose, 268 g of lactose ("Pharmatose 200M", product of DFE Pharma) and 12 g of hydroxypropylmethyl cellulose ("TC-5E", product of Shin-Etsu Chemical). They were mixed preliminarily for one minute at a blade rotational speed of 450 rpm and a chopper rotational speed of 3000 rpm, then subjected to addition of 120 g of water, and kneaded for 3 minutes at a blade rotational speed of 450 rpm and a chopper rotational speed of 3000 rpm. The kneaded product was sifted through a sieve having an opening of 1.00 mm to obtain a granulation product. The granulation product was placed in a fluidized-bed granulation dryer ("Multiplex MP-01", product of Powrex) and dried under the conditions of an intake air temperature of 80° C. and an air flow of from 0.7 to 0.9 m$^3$/min until an exhaust air temperature reached 55° C. (the water content of the granulation product: from 1 to 2% by weight). The average particle size of the dried granulation product was determined using the analytical sieving method described in "General Test" of the Japanese Pharmacopoeia Sixteenth Edition. The results are shown in Table 1.

(2) Tableting

The 100 parts by weight of the above-obtained granulation product were subjected to addition 0.5 part by weight of magnesium stearate as a lubricant, mixed, and tableted by a rotary tableting machine ("VIRGO", product of Kikusui Seisakusho) at a tableting pressure of 10 kN (about 200 MPa) and a tableting speed of 20 rpm to obtain a tablet having a diameter of 8 mm, a curvature radius of 12 mm, and a tablet weight of 200 mg.

As the hardness of the tablet, the maximum breaking strength was measured at which the tablet was broken when a load was applied to the tablet in a diameter direction thereof at a speed of 1 mm/sec by using a tablet hardness tester ("TBH-125", product of ERWEKA). The disintegration time was determined using a tablet disintegration tester ("NH-1HM", product of Toyama Sangyo) in accordance with the Disintegration Test (test liquid: water, without use of an auxiliary disk) of the Japanese Pharmacopoeia Seventeenth Edition. The results are shown in Table 1.

TABLE 1

| | low-substituted hydroxypropyl cellulose | | | | | granulation product | tablet | |
|---|---|---|---|---|---|---|---|---|
| | hydroxypropoxyl content (% by weight) | water-soluble content (% by weight) | maximum-torque-generating ratio | average particle size (μm) | alkali viscosity (mPa · s) | average particle size (μm) | tablet hardness (N) | disintegration time (min) |
| Example 1 | 10.8 | 1.4 | 4.4 | 61 | 62 | 215 | 53 | 3.4 |
| Example 2 | 10.9 | 1.8 | 4.0 | 58 | 60 | 250 | 56 | 4.5 |
| Example 3 | 8.1 | 1.3 | 3.8 | 54 | 60 | 251 | 52 | 4.0 |
| Example 4 | 13.8 | 1.8 | 4.6 | 60 | 64 | 235 | 60 | 4.2 |
| Comp. Ex. 1 | 10.9 | 2.2 | 3.6 | 55 | 58 | 335 | 58 | 5.7 |
| Comp. Ex. 2 | 10.8 | 1.1 | 2.9 | 40 | 52 | 429 | 56 | 8.6 |
| Comp. Ex. 3 | 10.9 | 3.5 | 2.6 | 39 | 54 | 533 | 60 | 10.9 |
| Comp. Ex. 4 | 11.2 | 3.9 | 2.0 | 50 | 7 | 668 | 94 | 60.7 |

In Examples 1 and 2 in which the water-soluble content was less than 2% by weight and the maximum-torque-generating ratio was from 3 to 5, each of the granulation products thus obtained had an adequate particle size and excellent tablet hardness and disintegration time. It is evident from the results of Examples 3 and 4 that granulation products having adequate particle sizes and tablets having excellent hardness and disintegration time can be obtained, regardless of the degree of substitution of hydroxypropoxyl groups.

In Comparative Example 1 in which the water-soluble content was 2% by weight or more, the disintegrability was inferior to those in Examples 1 to 4 because the water-soluble component dissolved and generated viscosity during disintegration of the tablet, thereby inhibiting water conduction into the tablet.

In Comparative Example 2, the water-soluble content could be reduced by increasing the amount of hot water used for washing, but even when the water-soluble content was reduced, the maximum-torque-generating ratio was less than 3 so that the granulation product had a large particle size due to excessive acceleration of granulation and the disintegration time became longer.

It is evident from these findings that to obtain a tablet excellent in hardness and disintegration time, the water-soluble content should be less than 2% by weight and the maximum-torque-generating ratio should be from 3 to 5.

Further, in Comparative Examples 3 and 4 in which the water-soluble content was 2% by weight or more and the maximum-torque-generating ratio was less than 3, the granulation was accelerated more excessively so that the disintegration time became longer than those in Comparative Examples 1 and 2. Particularly in Comparative Example 4, a drastic delay in disintegration time was observed.

The invention claimed is:

1. Low-substituted hydroxypropyl cellulose having a hydroxypropoxyl content of from 5 to 16% by weight and a water-soluble content at 25° C. of less than 1.5% by weight, wherein a weight ratio of water to the low-substituted hydroxypropyl cellulose giving a maximum torque is from 3 to 5 as determined while adding one part by weight of water per minute to one part by weight of the low-substituted hydroxypropyl cellulose under mixing with biaxial mixing blades.

2. The low-substituted hydroxypropyl cellulose according to claim 1, having an alkali viscosity at 20° C. of from 20 to 120 mPa·s, wherein the alkali viscosity means a viscosity of a 2% by weight solution of the low-substituted hydroxypropyl cellulose in a 10% by weight aqueous sodium hydroxide solution.

3. The low-substituted hydroxypropyl cellulose according to claim 1, having a volume-average particle size of from 30 to 100 μm as measured by a dry laser diffraction method.

4. The low-substituted hydroxypropyl cellulose according to claim 1, wherein a mixing blade on one axis of the biaxial mixing blades is rotated at 60 rpm with a peripheral velocity of 0.72 m/minute and a mixing blade on the other axis of the biaxial mixing blades is rotated at 30 rpm with a peripheral velocity of 0.36 m/minute.

5. A solid preparation, comprising the low-substituted hydroxypropyl cellulose of claim 1.

6. The solid preparation according to claim 5, having a dosage form of a tablet, granules, fine granules or a capsule.

7. A method for producing low-substituted hydroxypropyl cellulose of claim 1, comprising the steps:
   pulverizing starting low-substituted hydroxypropyl cellulose having a hydroxypropoxyl content of from 5 to 16% by weight into low-substituted hydroxypropyl cellulose powder having a volume-average particle size of from 30 to 100 μm as measured by a dry laser diffraction method; and
   classifying the low-substituted hydroxypropyl cellulose powder to remove therefrom small particles having a volume-average particle size of less than 30 μm as measured by the dry laser diffraction method.

8. A method for producing a granulation product of the low-substituted hydroxypropyl cellulose, comprising the steps of:
   blending the low-substituted hydroxypropyl cellulose of claim 1, a drug, and water or a water-soluble binder solution to obtain a mixture; and
   granulating the mixture.

* * * * *